US009332322B2

(12) United States Patent
Niemeyer et al.

(10) Patent No.: US 9,332,322 B2
(45) Date of Patent: May 3, 2016

(54) MULTIMODAL CLIMATE SENSOR NETWORK

(75) Inventors: Greg Niemeyer, Berkeley, CA (US);
Reza Naima, San Francisco, CA (US);
Antero Garcia, Fort Collins, CO (US);
Eric Hugh Kaltman, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 512 days.

(21) Appl. No.: 13/520,151

(22) PCT Filed: Dec. 29, 2010

(86) PCT No.: PCT/US2010/062448
§ 371 (c)(1),
(2), (4) Date: Oct. 23, 2012

(87) PCT Pub. No.: WO2011/090763
PCT Pub. Date: Jul. 28, 2011

(65) Prior Publication Data
US 2013/0038470 A1 Feb. 14, 2013

Related U.S. Application Data

(60) Provisional application No. 61/290,628, filed on Dec. 29, 2009.

(51) Int. Cl.
*G08C 19/04* (2006.01)
*H04Q 9/00* (2006.01)
*G01N 33/00* (2006.01)

(52) U.S. Cl.
CPC ............. *H04Q 9/00* (2013.01); *G01N 33/0075* (2013.01); *G01N 33/0036* (2013.01); *H04Q 2209/43* (2013.01); *H04Q 2209/845* (2013.01)

(58) Field of Classification Search
CPC ................................ F24F 11/0009; G01N 1/26
USPC .......................... 340/540, 584, 539.1, 870.11
See application file for complete search history.

(56) References Cited

U.S. PATENT DOCUMENTS

| 4,716,536 A | * | 12/1987 | Blanchard | ........... G01F 25/0061 340/620 |
| 5,255,556 A | * | 10/1993 | Lobdell | ................ G01N 1/2273 340/602 |

(Continued)

FOREIGN PATENT DOCUMENTS

| CN | 1588896 | 3/2005 |
| EP | 0812270 | 5/2003 |

(Continued)

OTHER PUBLICATIONS

Office Action, Chinese Patent Application No. 201080064328.X, Jul. 22, 2013, 17 pages.

(Continued)

*Primary Examiner* — Fekadeselassie Girma
*Assistant Examiner* — Rufus Point
(74) *Attorney, Agent, or Firm* — Perkins Coie LLP

(57) ABSTRACT

Techniques and systems are disclosed for monitoring multiple indoor and outdoor climate parameters and wirelessly transmitting the monitored data to a network for on-line analysis and dissemination. In one aspect, a monitoring device includes multiple sensors to monitor air quality modalities and generate corresponding monitored air quality data. The monitoring device includes a processor in communication with the multiple sensors to receive and process the monitored air quality data generated from the multiple sensors. Additionally, the monitoring device includes a display unit in communication with the processor to display the processed air quality data. The monitoring device includes a data communication unit to transmit the processed air quality data to a server. The server stores and optimizes the data through cross-calibration and makes the data available to persons who have purchased the monitoring devices and who wish to share the data in a social network.

24 Claims, 12 Drawing Sheets

(56) References Cited

U.S. PATENT DOCUMENTS

| | | | | |
|---|---|---|---|---|
| 5,394,934 | A * | 3/1995 | Rein | F24F 11/0009 165/200 |
| 5,428,964 | A * | 7/1995 | Lobdell | F24F 11/0009 236/44 C |
| 6,782,351 | B2 * | 8/2004 | Reichel | G01N 33/0075 340/501 |
| 7,131,767 | B2 * | 11/2006 | Socci | G01K 7/42 365/211 |
| 8,058,991 | B2 * | 11/2011 | Zajac | G01D 21/02 340/426.28 |
| 8,674,842 | B2 * | 3/2014 | Zishaan | F24F 11/0017 340/309.16 |
| 2003/0051023 | A1 * | 3/2003 | Reichel | G01N 33/0075 709/223 |
| 2005/0154494 | A1 * | 7/2005 | Ahmed | G05B 15/02 700/275 |
| 2006/0045168 | A1 * | 3/2006 | Socci | G01K 7/42 374/163 |
| 2006/0173579 | A1 * | 8/2006 | Desrochers | G01N 1/26 700/276 |
| 2007/0067063 | A1 * | 3/2007 | Ahmed | F24F 11/001 700/275 |
| 2007/0120652 | A1 * | 5/2007 | Behnke | G08B 25/14 340/286.01 |
| 2008/0266079 | A1 * | 10/2008 | Lontka | G08B 7/06 340/539.13 |
| 2009/0027196 | A1 * | 1/2009 | Schoettle | G08B 21/0469 340/541 |
| 2009/0040042 | A1 * | 2/2009 | Lontka | G08B 7/06 340/539.13 |
| 2009/0135006 | A1 * | 5/2009 | Schoettle | G08B 13/00 340/540 |
| 2009/0195349 | A1 * | 8/2009 | Frader-Thompson | G01D 4/002 340/3.1 |
| 2010/0102973 | A1 * | 4/2010 | Grohman | G05B 23/0272 340/584 |
| 2010/0141426 | A1 * | 6/2010 | Zajac | G01D 21/02 340/539.1 |
| 2010/0156632 | A1 * | 6/2010 | Hyland | G08B 25/08 340/540 |
| 2011/0231320 | A1 * | 9/2011 | Irving | G06Q 30/00 705/80 |
| 2011/0316699 | A1 * | 12/2011 | Arunachalam | G08B 21/14 340/540 |
| 2013/0021160 | A1 * | 1/2013 | Sid | B60K 28/10 340/632 |

FOREIGN PATENT DOCUMENTS

| | | |
|---|---|---|
| JP | H11504585 | 4/1999 |
| KR | 100177581 | 4/1999 |
| KR | 1020060102051 | 9/2006 |

OTHER PUBLICATIONS

Office Action, Chinese Patent Application No. 201080064328.X, Jun. 13, 2014, 8 pages.

International Search Report and Written Opinion, PCT Application No. PCT/US2010/062448, Aug. 18, 2011, 9 pages.

* cited by examiner

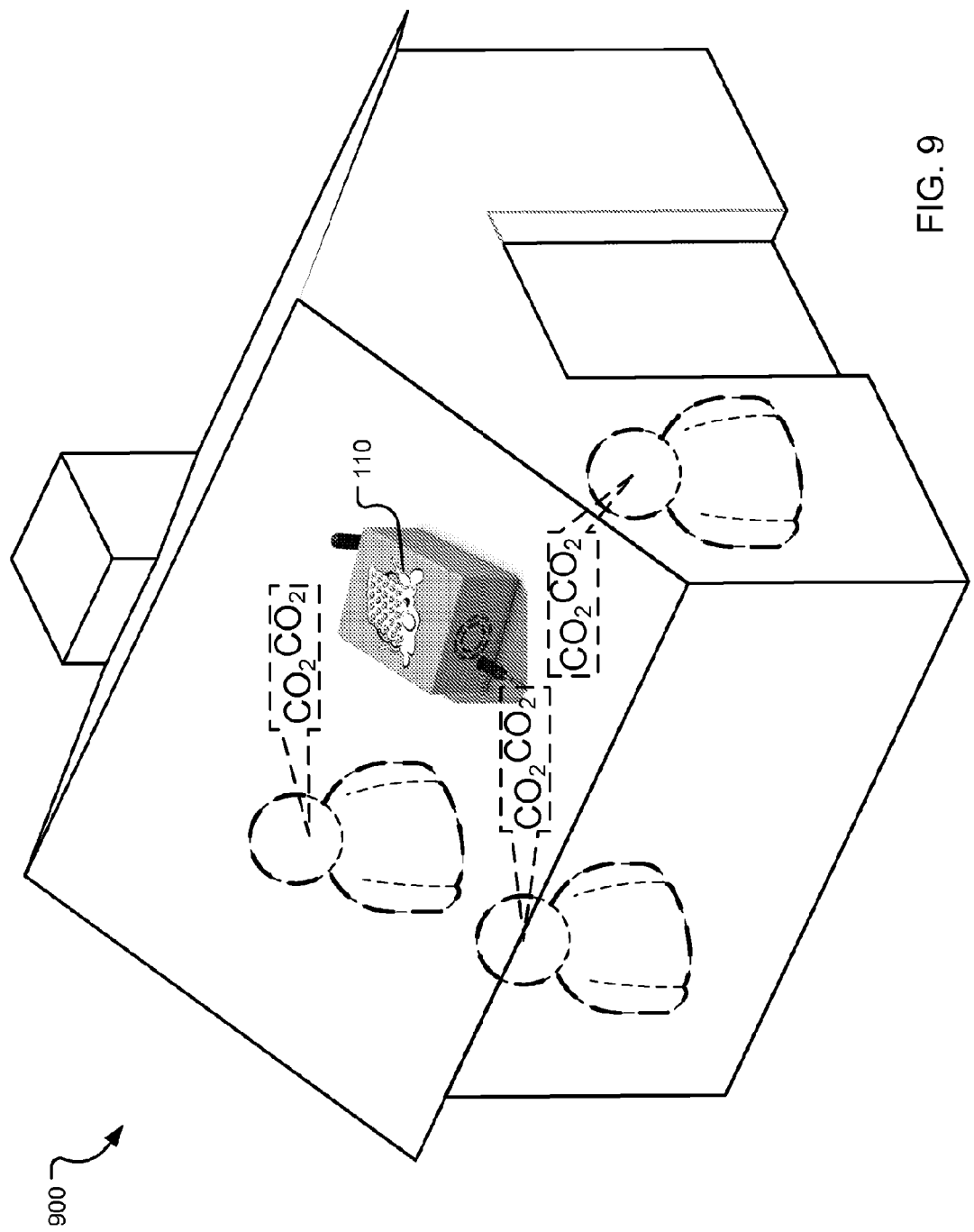

MULTIMODAL CLIMATE SENSOR NETWORK

CLAIM OF PRIORITY

This application is a 35 USC 371 National Stage application of International Application No. PCT/US2010/062448, filed on Dec. 29, 2010, which claims priority to U.S. Provisional Patent Application No. 61/290,628 entitled "MULTIMODAL CLIMATE SENSOR NETWORK" filed with the U.S. Patent & Trademark Office on Dec. 29, 2009. The entire contents of the before-mentioned patent applications are incorporated by reference herein.

BACKGROUND

This application relates to monitoring the air quality.

Air quality monitors typically sense a single parameter of air quality each. The monitored data obtained from the air quality monitors are tied to HVAC systems to regulate or control the HVAC system. There are also portable types of monitors that are designed for air quality professionals. These portable monitors tend to be expensive, and are intended for short-term sampling. Other monitors such as smoke detectors operate as alarms with a specific threshold.

SUMMARY

Techniques, systems and apparatus are disclosed for implementing a Multi-modal Climate Sensor Network (MCSN) that can continuously monitor multiple indoor and outdoor climate parameters.

In one aspect, a monitoring device includes a sensor bay, which includes multiple sensors to monitor air quality modalities and generate corresponding monitored air quality data. A processor is in communication with the multiple sensors to receive and process the monitored air quality data generated from the multiple sensors. Also, a display unit is in communication with the processor to display the processed air quality data. Additionally, a data communication unit can transmit the processed air quality data to a server.

Implementations can optionally include one or more of the following features. In the monitoring device, the multiple sensors can include at least two selected from the following: a light sensor, a temperature sensor, a humidity sensor, a noise sensor, a $CO_2$ sensor, and a volatile organic compound (VOC) sensor. In the monitoring device, the sensor bay can include multiple circuit boards. Each sensor can be disposed on a corresponding one of the multiple circuit boards. In the monitoring device, the sensory bay can include interface slots to receive the multiple circuit boards with the corresponding sensors. Also, the interface slots can be configured to interchangeable receive different circuit boards with corresponding sensors. In the monitoring device, a display unit can be included to present a level of each monitored air quality modality. The display unit can include light emitting diodes (LEDs) arranged to show the level of each monitored air quality modality. The monitoring device can include a position detector to detect a change in a location of the monitoring device.

In another aspect, a system includes a server to receive and store monitored air quality data. Multiple monitoring devices are in communication with the server to monitor air quality modalities. Each monitoring device can include multiple sensors to monitor the air quality modalities and generate corresponding air quality data. A processor is in communication with the multiple sensors to receive and process the air quality data generated from the multiple sensors. A display unit is in communication with the processor to display the processed air quality data. A data communication unit transmits the processed air quality data to a server as the monitored air quality data; and a storage medium includes a cross-calibration program which factors data from one of the multiple sensors into calibration of other sensors.

Implementations can optionally include one or more of the following features. The server is configured to provide a Web interface to allow users to review the monitored air quality data from the multiple monitoring devices. The Web interface includes a first graphical user interface widget to organize the multiple monitoring devices into one or more groups. The graphical user interface widget to organize the multiple monitoring devices into one or more groups can include an indication of total pollution for each group; and a contribution of each monitoring device in each group. The Web interface can include a second graphical user interface widget to display a time-dependent pattern of at least one of the monitored air quality modalities. The Web interface can include a third graphical user interface widget to allow users to conduct on-line discussions.

In another aspect, a method can include receiving, at a server, monitored air quality data from each of multiple sensor devices. The monitored air quality data from at least one of the sensor devices can include multiple air quality modalities monitored using multiple sensors. At a cross-calibration system, information from one of the sensors is factored into calibration of other sensors to confirm accuracy of all sensors. At the server, the received monitored air quality data is stored. From the server, a graphical user interface is presented to receive user input to organize the received monitored air quality data into one or more groups. The received monitored air quality data from the multiple sensor device devices are organized into the one or more groups based on the received user input. The received monitored air quality data organized into one or more groups is displayed.

Implementations can optionally include one or more of the following features. Displaying the received monitored air quality data organized into the one or more groups can include displaying total pollution for each group; and displaying a contribution of each sensor device in each group to the total pollution. Displaying the received monitored air quality data organized into the one or more groups can include displaying a breakdown of the different air quality modalities. The multiple sensors can be configured to monitor at least two selected from the following: light, temperature, humidity, noise, CO2 and volatile organic compounds (VOC). The graphical user interface can include a widget to allow two or more users to conduct an on-line discussion. The graphical user interface can include a widget to organize the multiple monitoring devices into one or more groups. The graphical user interface widget to organize the multiple monitoring devices into the one or more groups can include an indication of total pollution for each group; and a contribution of each monitoring device in each group. The method can also include displaying a time-dependent pattern of at least one of the monitored air quality modalities.

The subject matter described in this specification potentially can provide one or more of the following advantages. The Multi-modal Climate Sensor Network (MCSN) system can be used to provide networked, collaborative indoor and outdoor monitoring of climate and air quality in homes, warehouses, offices, schools, stores, hotels, parking garages, enclosed vessels for air, sea and space travel and other sites where humans breathe. Additionally, the described MCSN system can implement multiple sensors to sense multiple parameters of air quality at a time. The monitored parameters of air quality can be broadcast to online social networks and shared with other users. Ambient displays can be provided to share the data. The MCSN system can provide continuous monitoring at a low cost and at increased accuracy through cross-calibration. Cross-calibration uses data from one sensor (for example, temperature) sensing to support the calibration of other sensors performance is subject to change as a function of temperature. Also, the MCSN system can convey patterns of human-to-air interaction patterns.

BRIEF DESCRIPTION OF THE DRAWINGS

FIG. 9 is an image 900 that shows users trying to increase the $CO_2$ level on a sensor device during game play.

Like reference symbols and designations in the various drawings indicate like elements.

DETAILED DESCRIPTION

The techniques and systems described in this application can be used to implement a Multi-modal Climate Sensor Network (MCSN) that can continuously monitor multiple indoor and outdoor climate parameters. The monitored data can be wirelessly transmitted to a network for on-line data analysis. For example, the monitored data can be shared in real time to social networking web sites for collaborative and game-based climate monitoring and assessment across geographic boundaries.

The MCSN can be implemented as a network of low-cost personal and hyper-local sensors to monitor multiple air quality parameters and make the data accessible online in formats akin to social networking and online games. For example, the MCSN can include local wirelessly enabled sensor units to monitor various forms of ambient air pollutants (CO, $CO_2$, Nox, PM 2.5, tVOC) and environmental parameters (temp, humidity, light, noise, vibration) for local display. The monitored data can be up-loaded to a central server for storage, historic trending, sharing with other users, and social interaction to share knowledge and empower people to change personal habits in the interest of health and climate change management. The sensors used in the MCSN can focus on recording patterns of human-air interactions. By performing continuous, private monitoring that can be shared via social networks, data can be provided to users to recognize their own actions and their impact on their environment.

Multi-Modal Climate Sensor Network (MCSN)

Figure 1A:
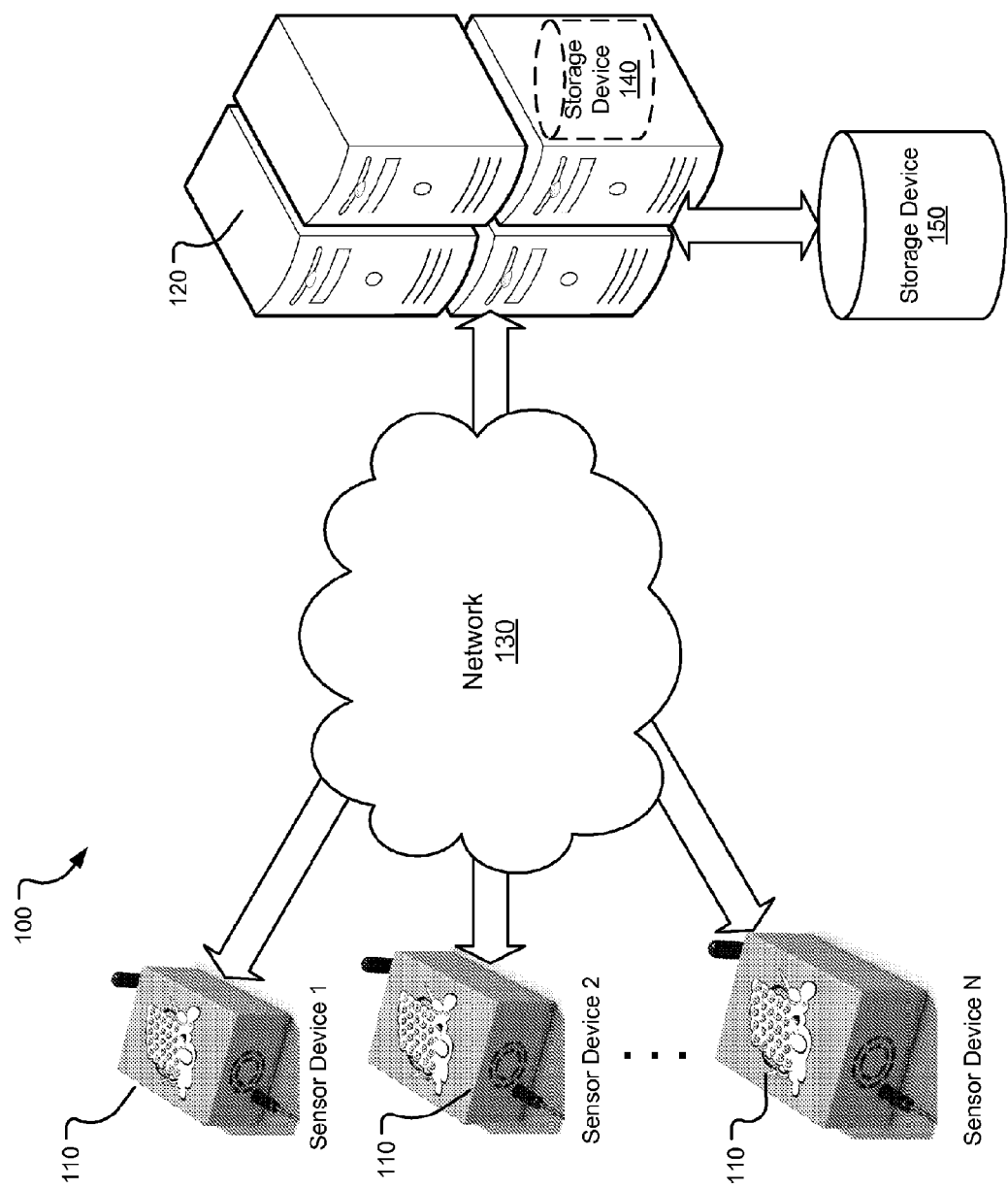
FIG. 1A is a block diagram showing an example representation of a Multi-modal Climate Sensor Network (MCSN) system.

FIG. 1A is a block diagram showing an example representation of a Multi-modal Climate Sensor Network (MCSN) system. The MCSN system 100 can include a monitor or sensor device 110 in communication with a server device 120 over a network 130. The MCSN system 100 can communicate with multiple sensor devices 110 that obtain sensor data from various locations. The network 130 can include various types of networks, such as the Internet, a virtual private network (VPN), a wide area network (WAN), a local area network (LAN or VLAN), etc. The sensor devices 110 can transmit sensor data wirelessly to the server device 120 over the network 130. The server device 120 can include a local storage device 140 to store data associated with sensor data received from the sensor devices 110. In addition, the server device 120 can communicate with an external storage device 150 to store the sensor data.

Sensor Devices

Figure 1B:
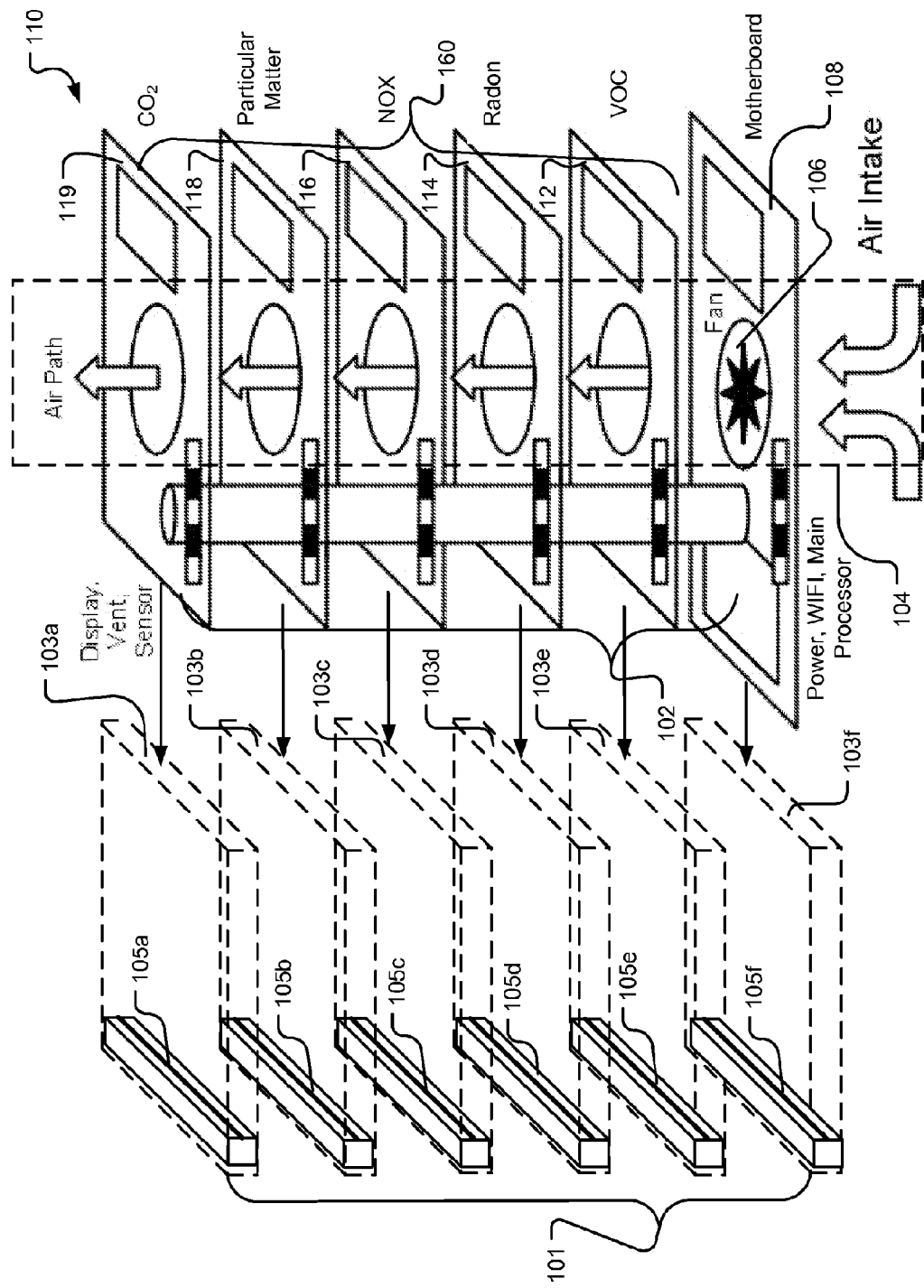
FIG. 1B is a diagram showing an example sensor device.

FIG. 1B is a diagram showing an example sensor device. The sensor device 110 can be implemented as a gas/particle/environmental sensor for monitoring ambient air of indoor or outdoor environment. Also, the sensor device 110 can operate as a communications device or an input/output device or both. The sensor device 110 can include common components including a power source, a clock, a data storage device, a display and a network communication protocol to upload data that support multiple sensors 160. For example, the sensor device 110 can integrate climate sensing, data display, storage and data transmission functions in one operational unit.

The sensor device 110 can include a sensory bay 101 with multiple interface slots 103a, 103b, 103c, 103d, 103e and 103f for receiving a number of circuit boards 102, such as a motherboard 108, various interchangeable boards, such as sensor boards 112, 114, 116, 118 and 119, display boards and telemetry boards. Each slot in the sensor bay includes an interface 105a, 105b, 105c, 105d, 105e or 105f for receiving and making an electrical connection with the corresponding circuit board. The interchangeable boards can connect to the motherboard, and the motherboard can relay messages between the various interchangeable boards, supply power and a constant air flow and pre-process data locally. The motherboard can include basic sensors, such as an accelerometer and a temperature/humidity sensor as a standard configuration, for example. Also, the motherboard can include a telemetry unit. All interchangeable sensor boards can share a common data and power bus which can be managed by the motherboard. The data, either raw or preprocessed, can be transmitted to a remote server using a transceiver (e.g., WiFi, WiMax, Ethernet, GSM, Bluetooth, etc.) which can be either located on the motherboard or present on one of the plug-in boards.

The sensor device 110 includes an air intake mechanism 104 to receive a sample of air into the sensor device 110. The air intake mechanism 104 can include a fan 106 that draws in a sample of air into the sensor device. The air intake mechanism 104 can be structured to form an air path for the sample of air to flow through the sensor device 110. As the air sample pass through the different sensor boards, the sensor boards can detect the corresponding gas, particles, environmental matters, etc. in the sample.

The motherboard 108 can include a microprocessor that polls the individual interchangeable boards to determine the nature of each board and determine if the boards are sources (e.g., sensors, telemetry that obtains data) or output devices (e.g., data transmission, visual and aural displays). In the example shown in FIG. 1B, the sensors 160 are implemented using multiple interchangeable sensor boards 112, 114, 116, 118 and 119 that can present the motherboard 108 with analog signals corresponding to the monitored sensor data, and the motherboard 108 can digitized the analog signals using a microcontroller, for example. Also, the sensor boards 112, 114, 116, 118 and 119 can present digital signals corresponding to the monitored sensor data to the motherboard 108. The digital signals can be generated by corresponding sensor elements or by an analog-to-digital converter (ADC) included in the sensor boards 112, 114, 116, 118 and 119.

The motherboard 108 and the individual interchangeable boards, such as the sensor boards 112, 114, 116, 118 and 119 can be configured by using a telemetry interface. For example, the user can connect to the motherboard directly, or by configuring options on a backend server. The remote server can convey data to the motherboard 108 by means of a push or pull mechanism determined by the nature of the telemetry mechanism used. Based on the installed boards and the external configuration, the microprocessor in the motherboard 108 can coordinate querying data from the sensor boards or the sensors built into the motherboard 108, and send the appropriate data to the visualization boards and/or the telemetry interface(s) (located in the interchangeable boards or built-in to the motherboard). The data can be sent using a serialized format, or encapsulated in a higher level protocol such as XML. Besides managing information, the motherboard can deal with power management issues, such as controlling the sampling rate of sensors and putting the sensors into a low power state when not used.

The interchangeable sensor boards 112, 114, 116, 118 and 119 can allow users to implement custom combinations of sensors. For example, an Asthma patient can select a sensor device a nitrogen oxide (NOX) sensor 116, a radon sensor 114, a volatile organic compound (VOC) sensor 112, a humidity sensor, a particulate matter sensor 118 and a $CO_2$ 119 sensor. When the user's needs change, the user can implement a new sensor to augment or replace old ones. Some sensors may have a limited lifespan (e.g., 2 years), and thus may need to be replaced periodically. Some sensors may need to be occasionally re-calibrated. Additionally, the sensor boards can be replaced with updated boards.

The sensor device 110 is agnostic to a specific communications mechanism, and can implement the interchangeable boards to designate different communication mechanisms. The MCSN monitoring device can be implemented as a wireless or wired Ethernet-based air quality device, a wireless cell phone-based air quality device or both. For the cell phone-based device, SMS communications, which uses a text messaging service plan, can be used. For the wired or wireless Ethernet-based device, Ethernet communications systems that do not incur per-unit operating costs can be used.

In some implementations, one interchangeable board can be populated with a GSM cell modem and a local microcontroller that can take a stream of data, pack it and, and transmit it via the cell modem. Another board can be populated with an Ethernet module and can present the user with an RJ45 connector to relay data to a remote server. This configuration allows for the ability of the sensor to have redundant telemetry mechanisms, and to support yet unavailable communications mechanism such as WiMax.

When the sensor device 110 is used in a stationary location, the user can supply the location details via a web interface. As described above, the sensor device 110 can include an accelerometer on a communications board to record vibrations and indicate a change in the position of the sensor device 110. Each change (that exceeds a user defined threshold for significance) in location of the sensor device 110 can trigger a prompt to be generated and sent to the user to enter the new location of the sensor device 110. When the sensor device 110 is used as a mobile, battery-powered unit, the sensor device 110 can be fitted with a global positioning satellite (GPS) board to provide geographic coordinates as a data stream relayed to the backend server (e.g., the central server) as though the geographic coordinates were a measured environmental parameter. The backend server can use the location information when processing the sensor data.

Figure 1C:
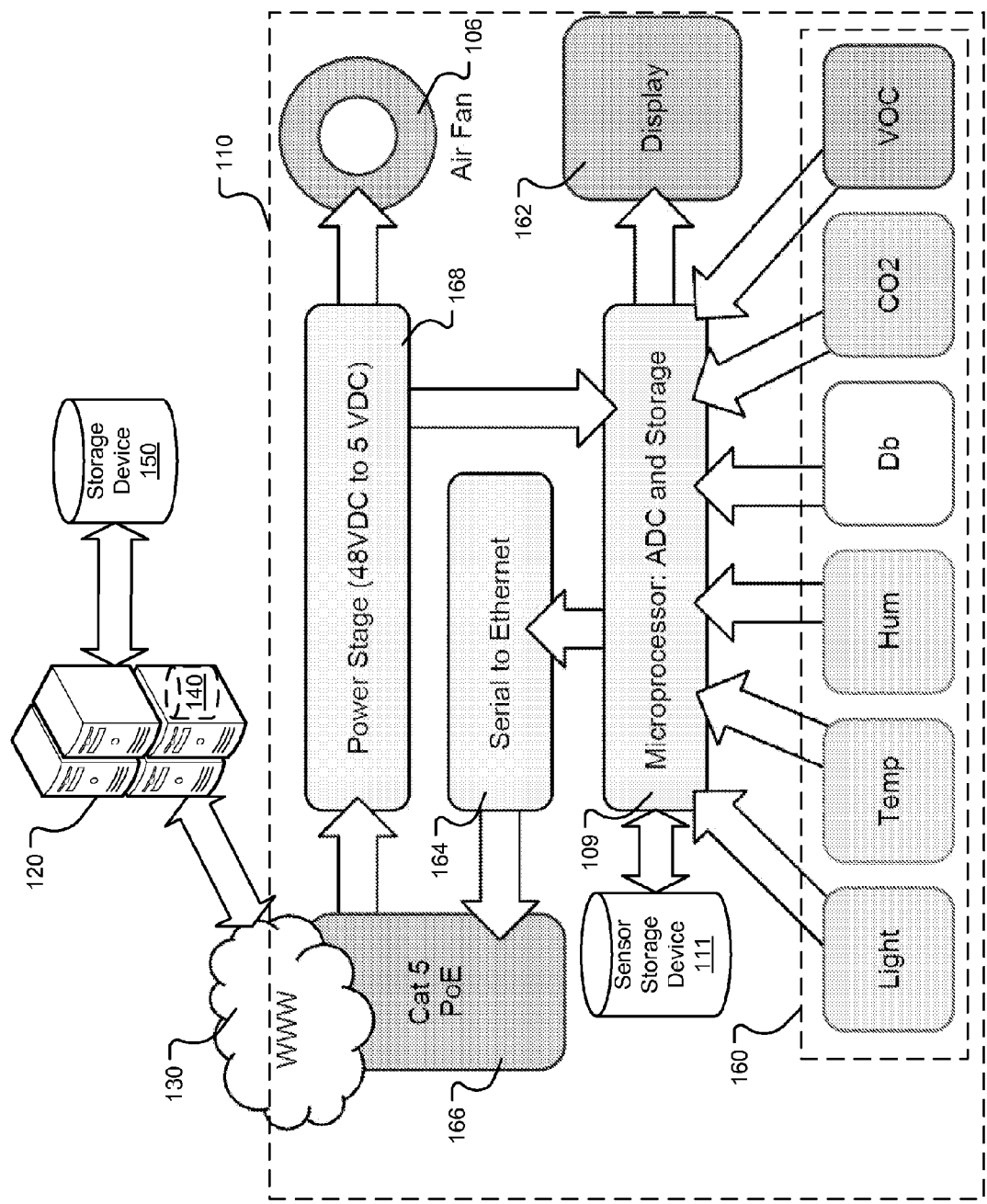
FIG. 1C is a block diagram showing communications among different components of a sensor device.

FIG. 1C is a block diagram showing communications among different components of a sensor device. As described in FIG. 1B, the sensor device 110 can include multiple sensors 160, such as light, temperature (Temp), humidity (Hum), sound (dB), $CO_2$ and VOC. The sensors 160 on the sensor boards 112, 114, 116, 118 and 119 can communicate with a microprocessor 109 located in the motherboard 108. The microprocessor 109 can include an ADC and a storage device. Also, a separate sensor storage device 169 can be included to be in communication with the microprocessor 109. The microprocessor 109 can communicate with a display unit 162 to output displayable data, such as the monitored data from the sensors 160. Additionally, the microprocessor 109 can provide a network connection for the sensor device 110 using a communication port 164, such as a serial network connection to the Ethernet. The Ethernet connection can be implemented using physical or wireless connections 166, such as a category 5 twisted pair connection. Using the network connection provided by the microprocessor 109, the sensor device 110 can communicate with a server 120 over a network, such as the Internet. Additionally, the sensor device 110 can include a power supply 168 that powers all components in the sensor device 110. For example, the power supply 168 can power the microprocessor, the various sensors 160 and the air fan 106.

Integrating Sensor Modalities

The sensor device 110 can be implemented to integrate multiple sensor functions, such as climate sensing, data display, storage and data transmission functions in one operational unit. The sensor device 110 can track multiple modalities of climate sensing including: (1) light, (2) temperature, (3) humidity, (4) noise, (5) $CO_2$, and (6) VOC (Volatile Organic Compounds). Additionally, the device can include vibration and particulate matter sensors.

These example modalities represent classic health and stress factors, can be fairly easy to measure, and can be directly affected by local human activity. A number of combinations of visible and invisible modalities can be incorporated into the sensor device 110. Users can verify the visible and audible modalities and gain confidence that the monitor is tracking the invisible modalities correctly. Additionally, the users can affect the read-out instantly by applying various input that affects the sensors, such as by shouting at the monitor (noise modality), shining a light at it (light modality), or holding a permanent marker under it. Such interactions can provide the users with the assurance that the sensor device is working and responding reliably to changes in the environment.

The light sensor can monitor natural light or artificial light. Additionally, the light sensor can monitor the effect of the natural and artificial lights on the circadian rhythm. The light sensor can also monitor and reveal human activity patterns. The temperature sensor can be used as a strong indicator of location (indoor/outdoor) and the presence of HVAC systems. The noise sensor can monitor and show human and machine activities. Also, the noise sensor can act as a strong indicator of environmental stress. $CO_2$ sensing can be used to show respiration, combustion, and sequestration, the full CO2 cycle. Volatile Organic Compounds sensing can show the presence of cleaning agents, gasoline, furniture, building materials, solvents, and alcohol.

Sensor Display

The sensor display can increase people's trust in the monitor, and establish an ambient presence which communicates air quality clearly when the user seeks the information, but which does not command inappropriate attention. The display unit can be configured to show any number of the sensor modalities. For example, five of the modalities with five level indicators can be displayed to keep the display clean and simple, even if the sensor device is tracking more than five modalities. The display unit can be configured to include no text to encourage the users to be more inclined to explain the display when the users show the display to other people. The low resolution of the levels supports an easy ambient reading that does not require reading numbers.

Figure 1D:
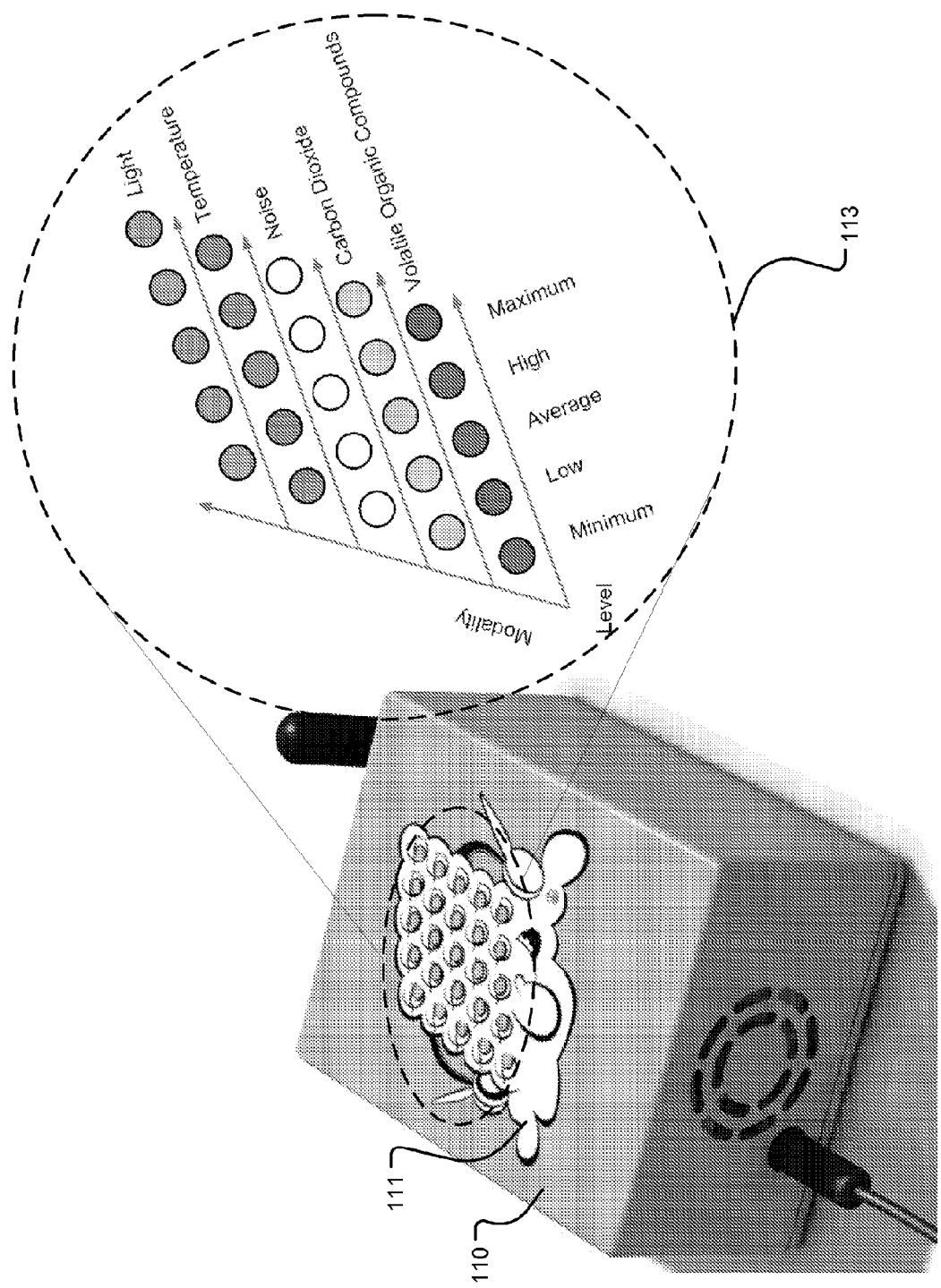
FIG. 1D shows an example sensor device with an LED light configuration for air quality display.

FIG. 1D shows an example sensor device with an LED light configuration for air quality display. The sensor device 110 can include a display unit 111 located on an external surface of the sensor device 110. For example, the external display unit 111 can include a display character (e.g., a cartoon cloud called Cloudy McPufferson) with LED "eyes" 113 that allows for a more ambient, intuitive and emotional reading of the sensor data. The sensor data can be transmitted using network communications to a website, where users can review and compare patterns of air pollution.

Figure 2:
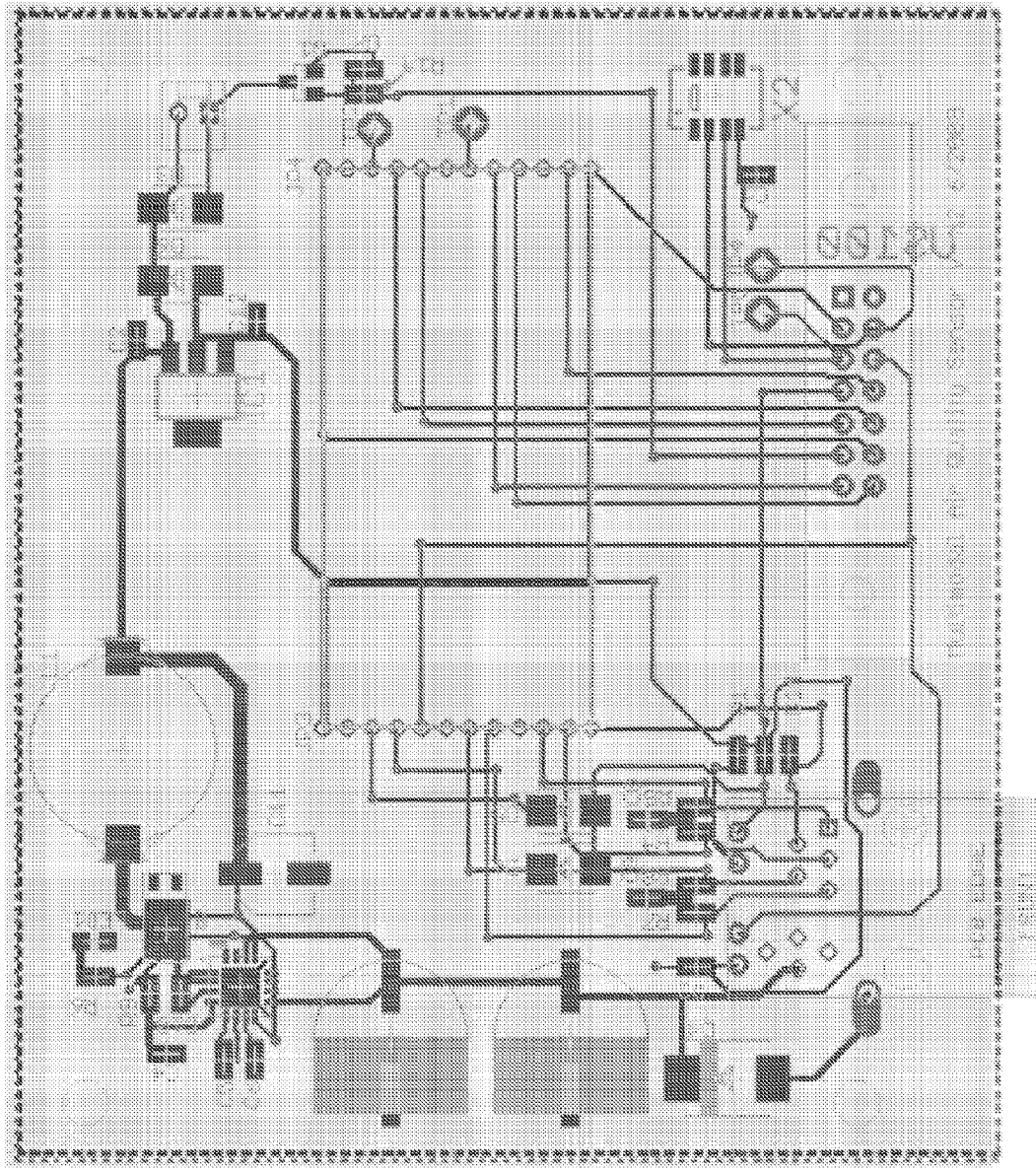
FIG. 2 is a diagram showing an example printed circuit board (PCB) for a power stage of a sensor device.
Figure 3:
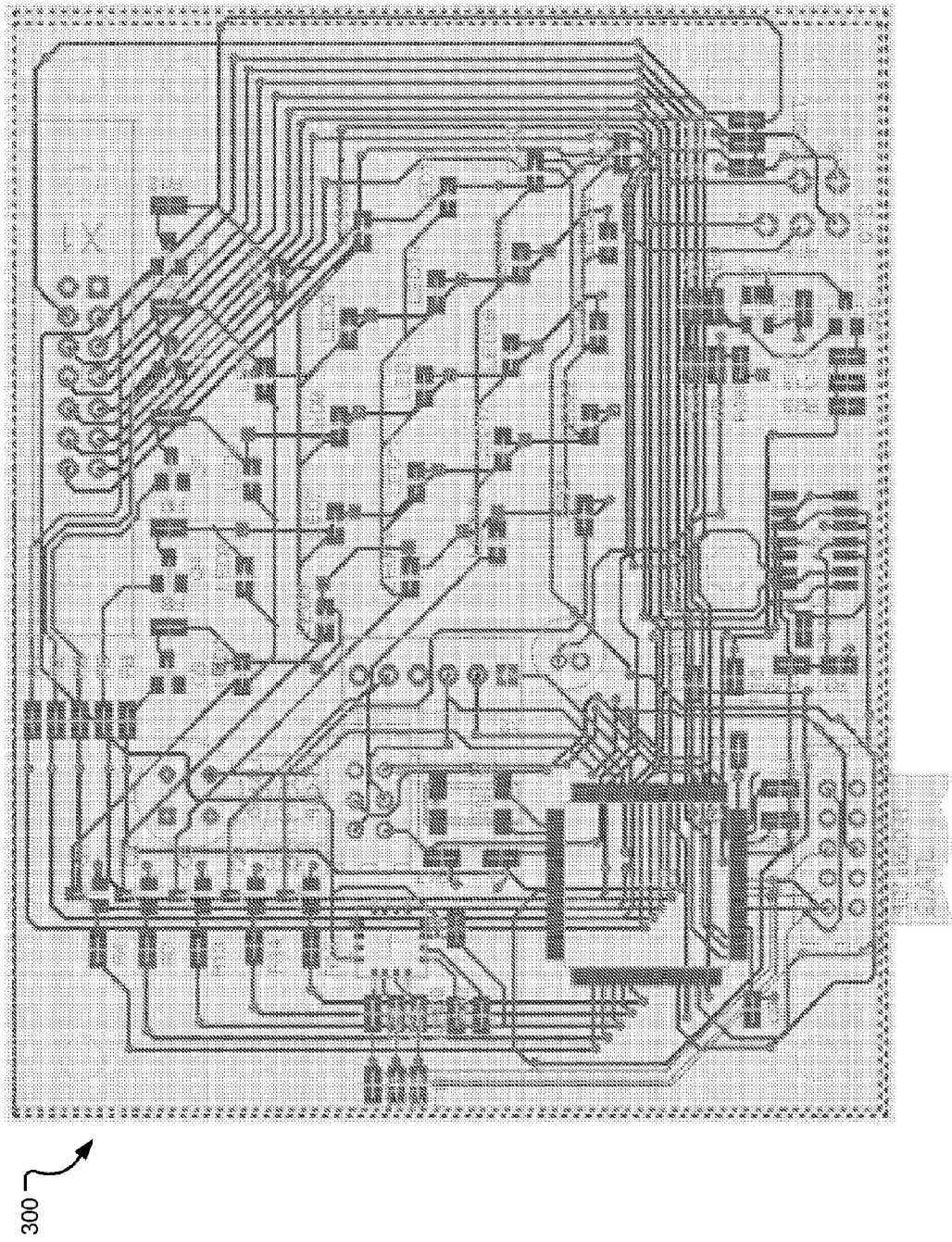
FIG. 3 shows a diagram showing an example PCB for a computation, sensor and display stage of a sensor device.

FIG. 2 is a diagram showing an example printed circuit board (PCB) for a power stage 200 of a sensor device. Also, FIG. 3 shows a diagram showing an example PCB for a computation, sensor and display stage 300 of a sensor device. The PCBs can be implemented to separate the power and communications board 200 from a sensing, processing and display board 300. An Atmel chip can be used to run the device's program and memory, for example. The two boards 200 and 300 can be stacked vertically to allow for airflow between the boards for both cooling and sampling.

Cross-Calibration Among Sensors

Additionally, each sensor device 110 can include a cross-calibration system that can determine the accuracy of all sensors in the sensor device 110 by factoring information from one sensor into continuous calibration of other sensors. Continuous monitoring calibration can include calibrating the sensors periodically at a set period of time (e.g., every minute, every hour, every day, etc. or calibrate at certain time teach day, etc.), calibrating the sensors each time a sensor reading is obtained, or calibrating each time the user or the server requests calibration. For example, data from the temperature sensor can be used to support the calibration of other sensors performance, and thus the other sensors can be subject to change as a function of temperature. Similar cross-calibration is possible for any of the sensors. The cross-calibration system can be implemented using a cross-calibration program stored in a storage device, such as the local sensor storage device 169 and executed by the central processor on the motherboard 108 or a microprocessor 109 on any of the sensor boards 112, 114, 116, 118 and 119. In addition, the cross-calibration system can be stored as a program on an external storage device 150 (or on a storage device 140 local to the server 120) in communication with the center server device 120 and executable by the central server device. Thus, the cross-calibration system can be performed locally on each sensor device 110 or centrally performed for all sensor devices 110 at the central server 120.

Central Server

The central server 120 receives individual sensor device data from the sensor devices 112, 114, 116, 118 and 119 and archives the data in a database of a storage device (e.g., 140 or 150). The server 120 can provide a web interface to allow users of the different sensor devices to review historic trends in their own data, and to recognize correlations between patterns of activity and patterns of pollution. The sensor data can be presented to the users in the framework of a social network. The social network allows users to share and comment on each others data. The MCSN effectively ties-in the dynamics of social interaction with air quality data evaluation. Driven by social interaction, users can increase awareness of air quality, share knowledge about the observation and management of personal air pollution (predominantly indoor air-pollution), and build clean air reputations for themselves.

Archiving and Historic Trending Capacity

The server 120 can accept data at any rate (i.e., once a day or 10 times a second) and the server 120 can store the data in a number of locations such as plain text files, XML files, or in one or more databases. To conserve space, historic data can be averaged where the averages are stored, and the original data can be discarded. The server 120 can share either the raw data or the processed/averaged data with the users. The raw data and the processed/averaged data can be accessed by a wide range of applications, such as graphing applications or web browsers to generate real-time visual displays. A historic trending application can allow users to review data from their own sensor devices at various temporal resolutions using a zooming function. The zooming function allows users to recognize patterns in air quality. The visualization interface can either be a separate application that connects to the server 120, static or dynamic web pages served from a server, or an application that runs inside the web browser such as flash, or as a widget that can be integrated into existing networks, such as Facebook.

Figure 4:
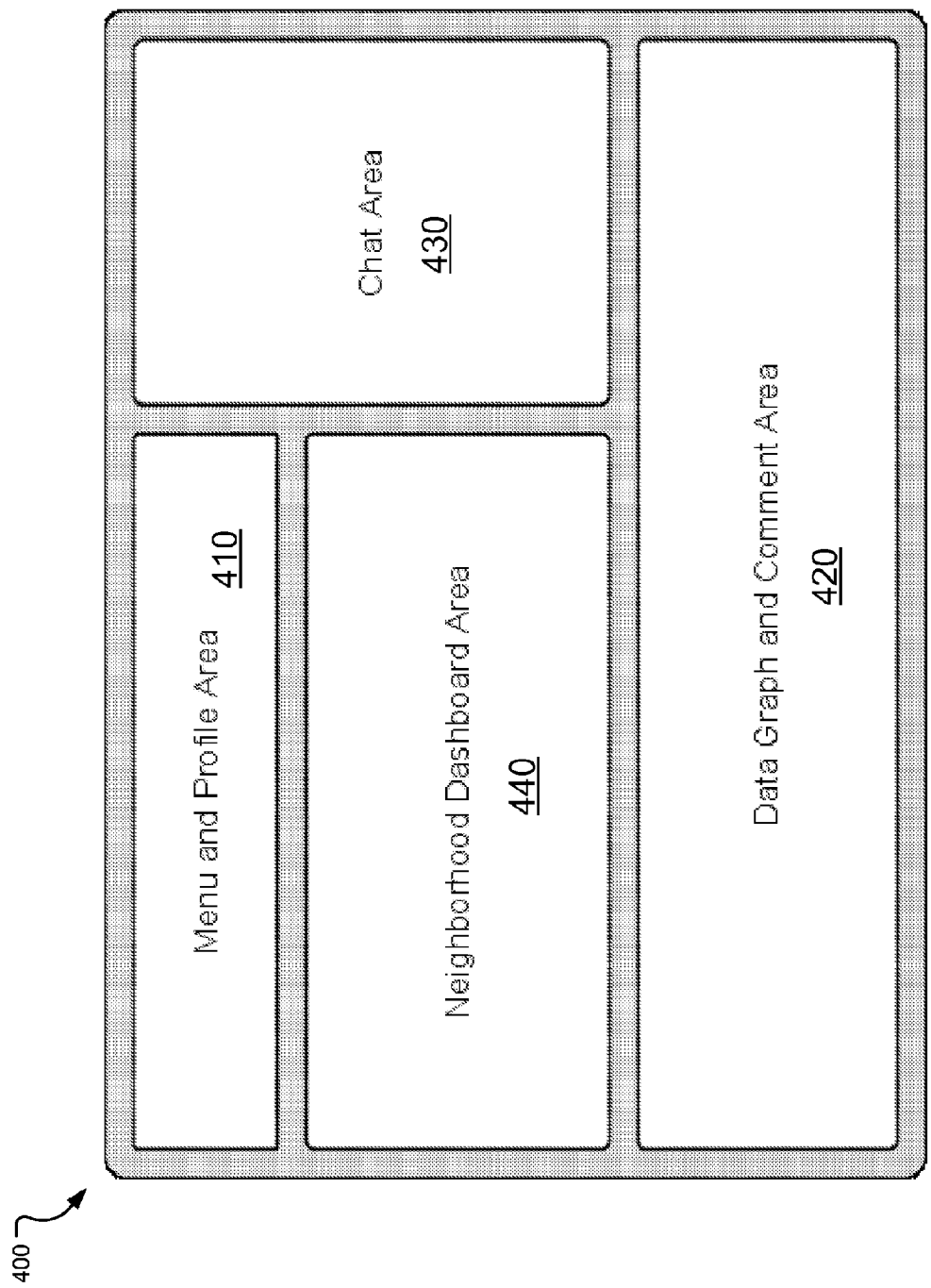
FIG. 4 is a diagram of an example interface for communicating between a sensor device and a server.

Ability to Review Other Sensor Device's Real-Time and Historic Readings:

FIG. 4 is a diagram of an example interface for communicating between a sensor device and a server. The server 120 can include a social air quality interface 200 that provides a profile and a login for each sensor unit user. The example shown in FIG. 4 represents an implementation of a Neighborhood Dashboard Online Social Network Interface. The interface 400 can include various areas configured to perform different functions. For example, the interface 400 can include a Profile and Menu Area 410 to maintain user profiles regularly with user information such as sensor location, interests, and air quality concerns. The sensor unit 110 associated with the corresponding user can complete the user profile with data from the sensor unit 110. Users can connect their profiles to other users' profiles and thereby create virtual neighborhoods of air quality monitors. These spontaneously created virtual neighborhoods can be based on geographic, professional, medical, social and other affinities.

Social Networking Format to Enable Users to Discuss and Post Q&A Regarding Observed Sensor Data and Facilitate Habit Change for the Realization of Better Local and Broad Based Air Quality Members of a virtual neighborhood of air quality monitors can review and comment on each other's data. The members can share advice about air quality and health issues. Additionally, the members can chat socially, and can collectively analyze and solve air quality problems. By organizing a community around the aggregated micro-data, the MCSN system can provide a platform for collaboration to address air quality issues, where users can build their reputations and become neighborhood leaders.

The interface 400 can include a Data Graph & Comment Area 420 to provide a forum for the users to collaborate by comparing each other's data to detect air quality patterns. Additionally, the interface 400 can include a Chat Area 430 to provide a forum for the users to support other users financially, intellectually or emotionally in solving their air quality issues, for example. These processes can be supported by a user interface with multiple windows to show online chat dialogue, images of sensor locations, pictures of users, and data graphs and charts simultaneously. Users can write text directly into each others data charts using editable fields in the Data Graph & Comment Area, for example.

The texts can either be comments, questions or answers. A reputation tracking system can track the number and ratings of these texts postings per user. The reputation tracking system can also track how many comments and questions a specific data stream generates. The data collected by the reputation tracking system can produce a class of metadata that establishes a user's credibility and reputation as a citizen scientist and as a neighborhood leader. With advanced status as a neighborhood leader, users can gain privileges such as starting a new neighborhood, raising funds to help other people solve air quality issues, and requesting changes in the design of the air quality monitoring services offered. Advanced users can also organize non-virtual real-world events, workshops, and air quality improvement calls for action on the site's calendar. The real world calls for action can be documented and tracked with a news tool in the Neighborhood Dashboard Area 440 of the interface 400. The news tool is linked to the air quality data charts, completing a feedback loop between measurement, analysis and remedies. Using this feedback loop, a correlation between a call for action and a measured air quality result can further increase a user's reputation. These reputation-based rewards can define the participation in the air quality network as a constantly more challenging and more rewarding social experience which keeps users engaged in the service indefinitely.

For example, a sensor device 110 can be placed in critical rooms in every house, office, school or factory and broadcast the monitored data from each location to a website hosted by a server, where users can compare, advice and support each other in addressing Indoor Air Quality issues. Through the website, users can also engage with each other through games that use air quality data as a part of the fun. For example, a social interface can be implemented to help users bond with air quality data, and motivate users to pursue permanent, original and independent transformations toward improving air quality.

Through the website, the users can review and compare data from monitors or sensor devices around the world, and advise each other about air quality. Thus, the website can provide a tool to allow users from different geographic locations to compare multi-modal air quality data with each other. Through this comparison, repeating patterns of pollution can become transparent. When users change their behaviors to influence these patterns of pollution, their reputation in the community of monitor hosts increases. This reward of increased social standing can provide a strong motivation for pursuing and maintaining behavioral change in the interest of air quality.

Figure 5:
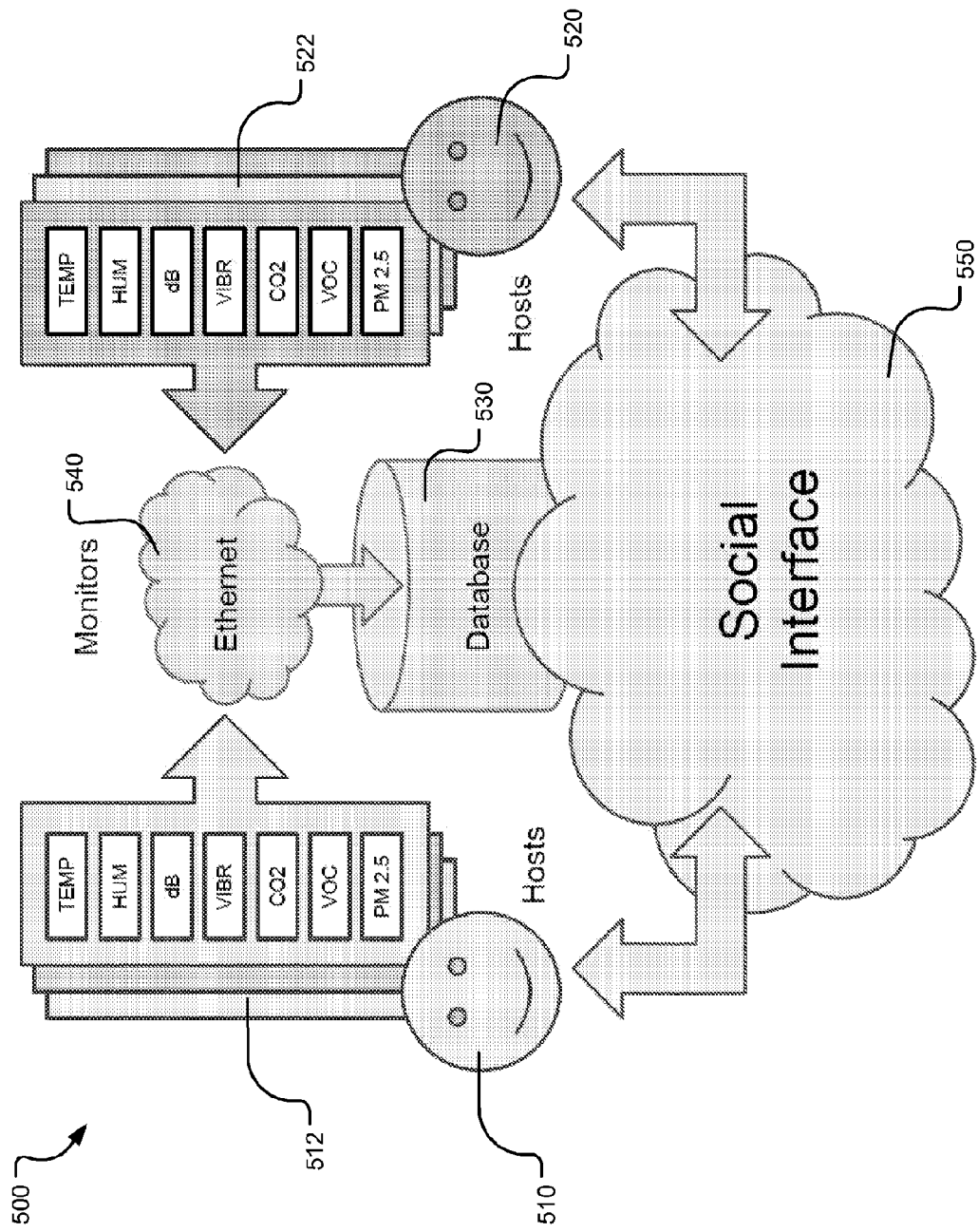
FIG. 5 is a diagram showing an MCSN with an example social interface for climate data schema.

FIG. 5 is a diagram showing an MCSN with an example social interface for climate data schema. The MCSN 300 includes various hosts or users 510 and 520 associated with corresponding sensor devices or monitors 512 and 522. The sensor devices 512 and 522 can perform continuous monitoring of multiple air quality parameters and transmit the monitored data to a server over a network, such as the Ethernet 540. The monitored data can be stored in a storage device, such as a database 530. Additionally, the users can communicate with a social interface 550 presented using a website, for example, to share the monitored data with other users.

As described above, social networking website can be implemented to allow users to review, compare and discuss their own air quality data with members in their virtual neighborhood. Each user can organize and create one or more virtual neighborhoods based on various categories, such as geography, professional activity, advocacy or affinity. A single user can be a member of multiple virtual neighborhoods. Each virtual neighborhood created by one or more users consists of the user's monitored data and the monitored data from other users' sensor devices included in the virtual neighborhood. Including a neighbor's data in one's neighborhood can include obtaining the permission of the host of the sensor device. Neighborhoods can also swap emission credits, or collect emission credits for trade with other neighborhoods. Emission credits occur when an individual user can decrease the emission of $CO_2$ or other pollutants relative to a historically established emission baseline. Such individual emission credits can be aggregated in a neighborhood to facilitate trading on the carbon offset market.

Figure 6:
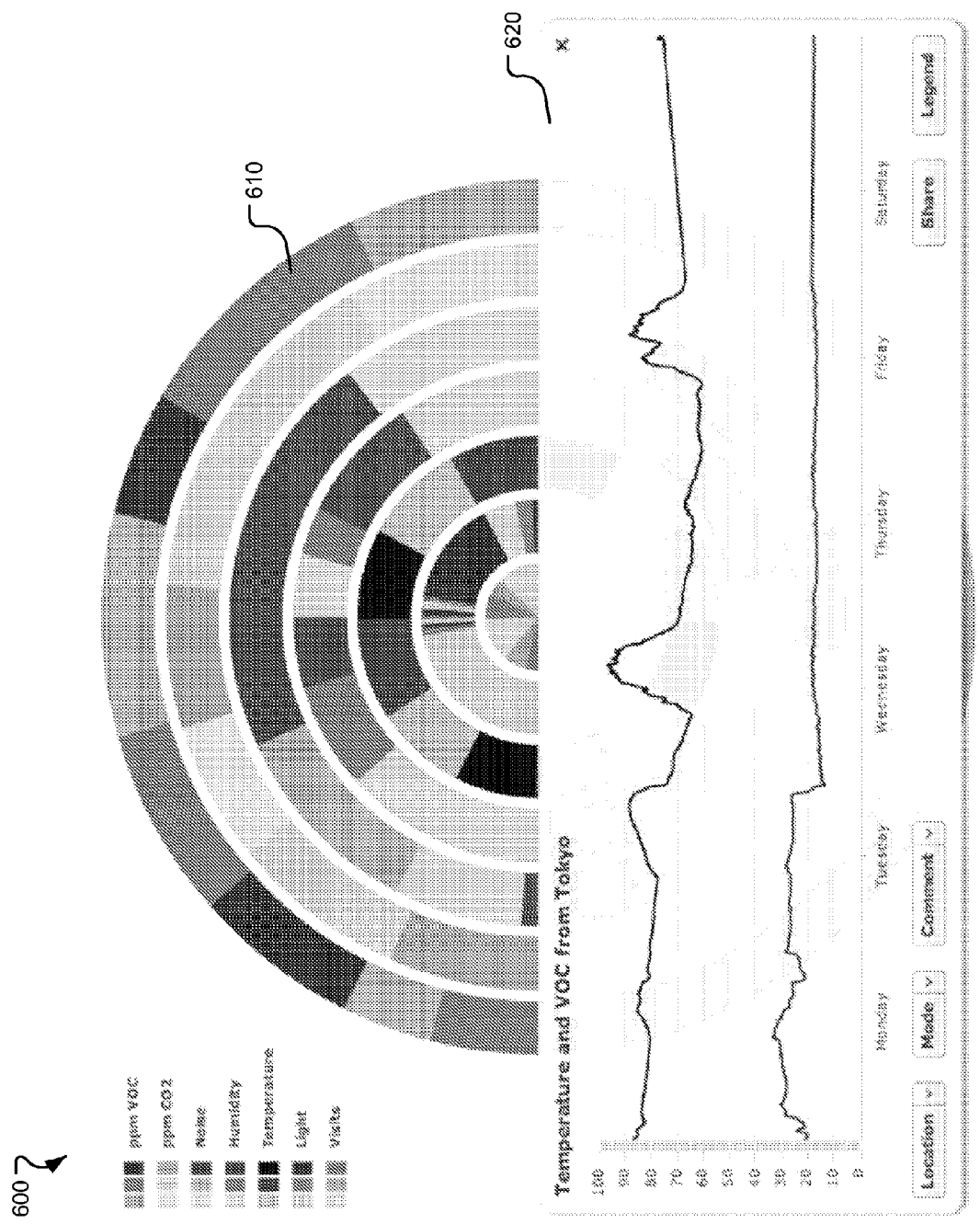
FIG. 6 is a screenshot shows an example neighborhood ring presented as a proportional graph.

FIG. 6 is a screenshot shows an example neighborhood ring presented as a proportional graph. The screen shot 600 includes a neighborhood ring 610 identifies the sensor devices included in a user's neighborhood and compares the contribution of each location as a percent of the neighborhood's total output. Clicking on the graph takes the user to a traditional time series curve graph window 620 which can reveal the pattern of a specific modality. In the time series curve graph window 620, users can compare data in different time frames, different locations and different modalities. Users can also comment on any monitor location and pursue social interactions concerning air quality. In the screen shot example shown in FIG. 6, the time series curve graph 620 can be used to compare temperature and VOC's.

On the social interface Web site, users can comment on their own data as well as on the data of their neighborhood members. The users can discuss unusual occurrences, pollution reduction strategies, health and safety questions, and of course they can play speculative, detective and other online games that are based on the neighborhood's data.

Figure 7:
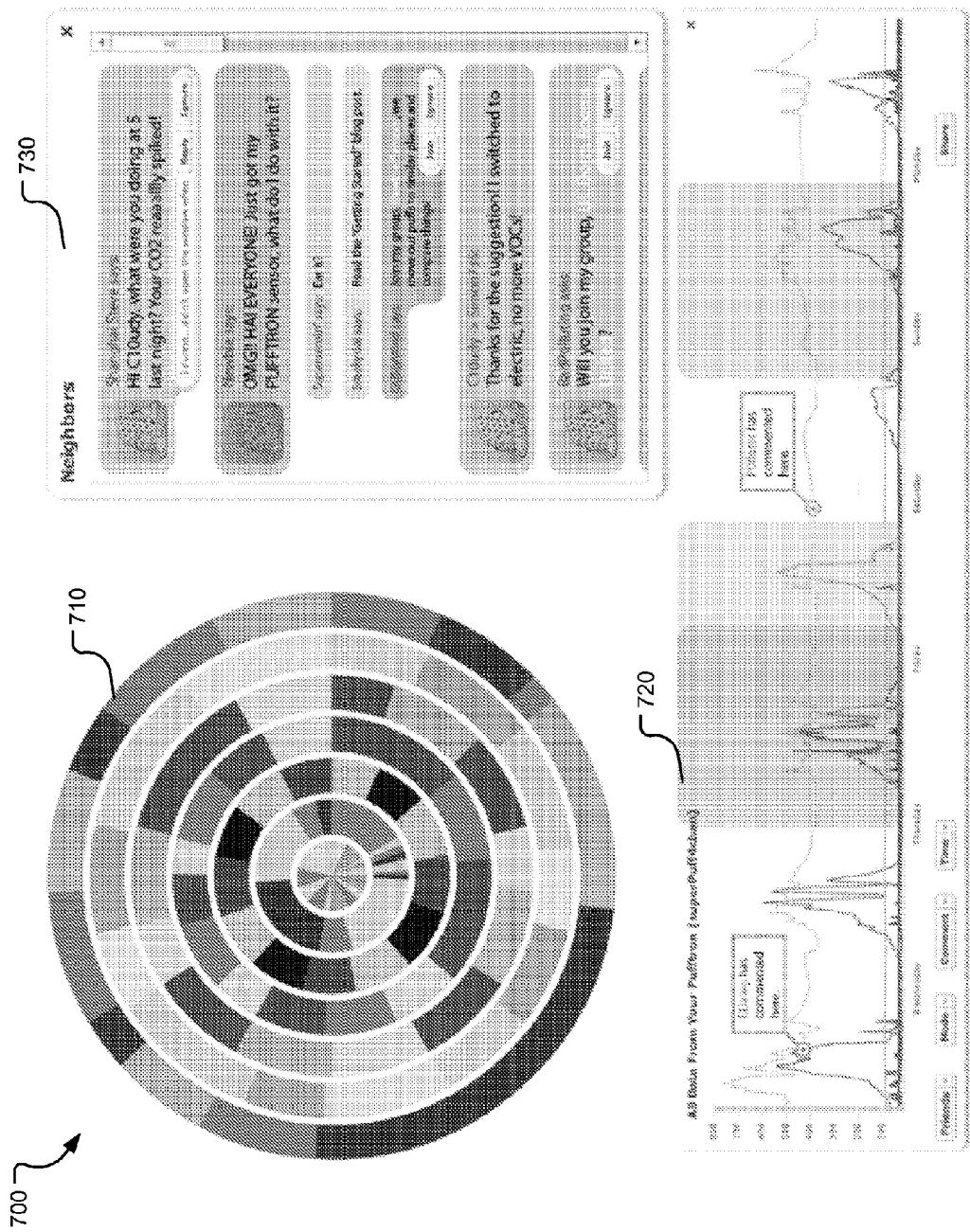
FIG. 7 is a screenshot showing air quality data with social interface (e.g., chat, comment and area of interest).

FIG. 7 is a screenshot showing air quality data with social interface (e.g., chat, comment and area of interest). The screenshot 700 includes a neighborhood ring 710 identifies the sensor devices included in a user's neighborhood and compares the contribution of each location as a percent of the neighborhood's total output. Additionally, a time series curve graph 720 shows the data compared in different time frames. Also, the screenshot 700 includes a chat window 730 to allow users to communicate with each other about an area of interest.

Figure 8:
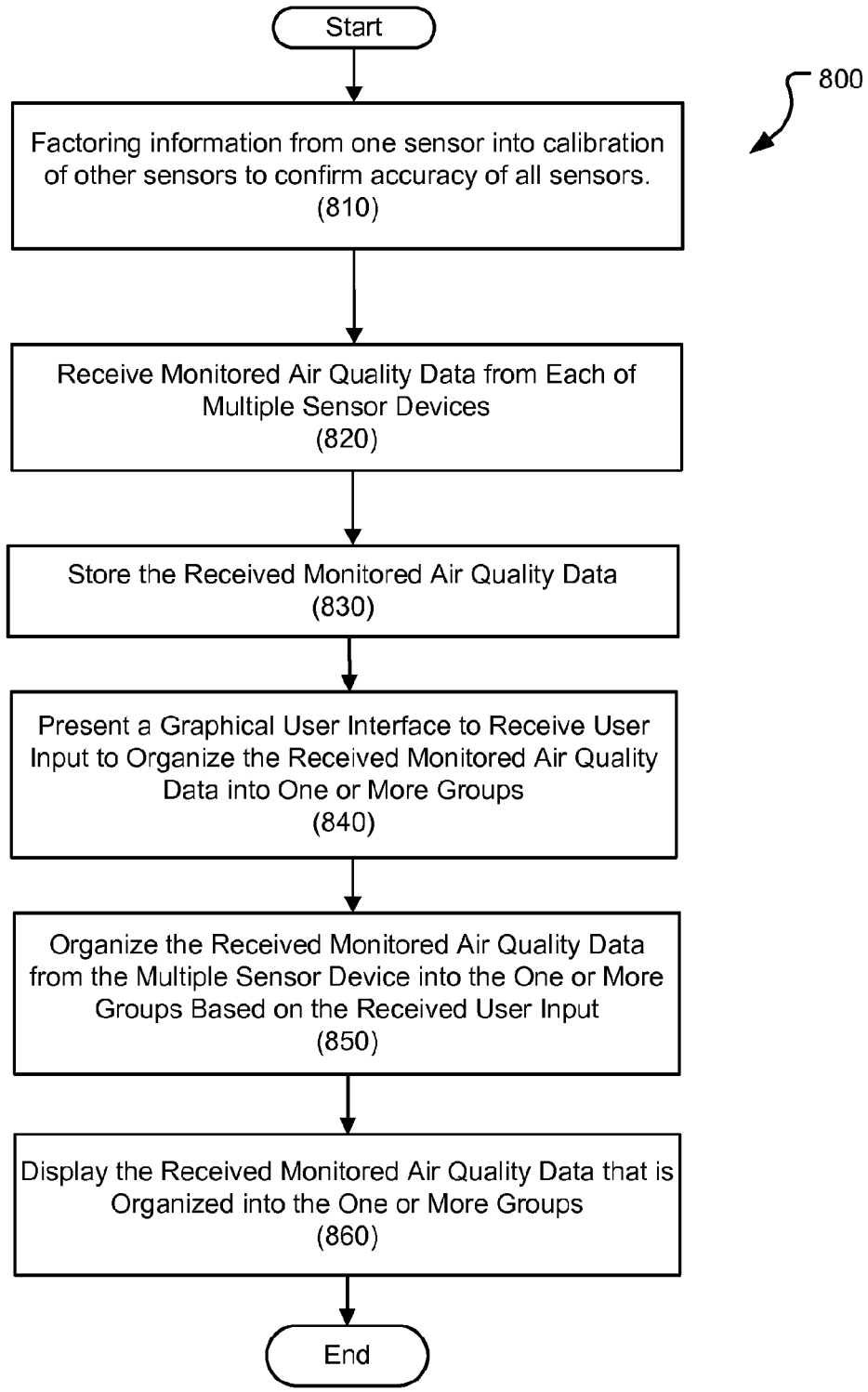
FIG. 8 is a process flow diagram showing a process for monitoring and sharing air quality modalities.

FIG. 8 is a process flow diagram showing a process 800 for monitoring and sharing air quality modalities. A cross-calibration system can factor information from one sensor into calibration of other sensors to confirm accuracy of all sensors (810). The calibration can be continuous as described above. The system can receive monitored air quality data from each of multiple sensor devices (820). The monitored air quality data received from each sensor device can include monitored data from multiple sensors that monitor different air quality modalities. The system can store the received monitored air quality data (830). The stored data can be analyzed for historic data tracking, for example. The system can present a graphical user interface to receive user input to organize the received monitored air quality data into one or more groups (840). The system can organize the received monitored air quality data from the multiple sensor device into the one or more groups based on the received user input (850). The system can display the received monitored air quality data that is organized into the one or more groups (860).

In displaying the received monitored air quality data into the organized one or more groups, the system can display the total pollution for each group. Also, a contribution of each sensor device in each group to the total pollution can be displayed. In displaying the received monitored air quality data into the organized one or more groups, the system can display a breakdown of the different air quality modalities. The multiple sensors can be configured to monitor at least two of light, temperature, humidity, noise, $CO_2$ or volatile organic compounds (VOC). Additionally, the graphical user interface can include a widget to allow two or more users to conduct a discussion.

Example of a Monitor with Users Trying to Increase the $CO_2$ Levels

A website can be implemented to provide a game board for an Alternate Reality Game. The game objective can include capturing as many hidden monitoring devices as possible for a team. FIG. 9 is an image 900 that shows users trying to increase the CO2 level on a sensor device during game play.

Case Studies Based on Original Embodiment

User 1: Utilizing a single in-home sensor unit, discovered that VOC levels spiked in home during late evening on a repeating basis. Correlated VOC levels with habit of burning paraffin wax candles during the evening. Switched to soy based candles and saw marked reduction in in-door VOC levels thereafter.

User 2: Utilizing single in-home sensor unit, discovered that household cleaning supplies were creating periodic spike in VOC levels within home on days when housekeeper came to work. Switched to "green" cleaning supplies and saw VOC level spikes abated.

User 3: Utilizing data from own and local area sensor units, discovered trend in local air pollution correlated to morning commute traffic at proximate roadway intersection. Altered habit of airing out the home in the morning, to airing out during the evening, realizing significant reduction in in-home CO levels.

User 4: Utilizing on-line portal, evaluated choices of day-care providers based upon monitored local air quality. Provided feedback to day-care providers with lesser quality air, prompting day-care provider to invest in air purification/filtration technology to remain competitive.

User 5: Unsure why their indoor air quality was consistently poor during winter months receives advice from another member of the central web site to check their home furnace. During follow-up inspection discover that central gas-heater's vent pipe was slightly dislodged, exhausting some products of combusting into attic space, which then migrated into living space on a gradual consistent basis during cooler months when the heater was in use. Repaired heater exhaust and saw marked reduction to in-home pollution levels.

User 6: Devices installed in hotels will demonstrate real time and historic air quality information which can empower consumers with more information when choosing a hotel.

User 7: An asthma patient has sensors at work, at home, and at a family member's home. Comparing air quality in the three locations, the user can determine which location is the healthiest at a given time, and the user can also observe air quality patterns to predict which locations will be healthy at what time.

User 8: A number of users have formed an air quality neighborhood because they all have children that attend the same school. They place sensors at the school and at their homes and notice that the time children travel to school coincides with the time of the worst daily air pollution. They petition the school to move the morning bell time by 30 minutes to reduce student exposure to pollution. As a result, asthma episodes among the school children drop by a significant percentage.

User 9: In reaction to recent news coverage about indoor air pollution in schools located near freeway corridors, a school teacher sets-up her classroom's air-pollution sensor to broadcast reports via 'Twitter' messages. Via his monthly email update, the teacher informs the parents that the classroom sensor has a Twitter account. This is especially convenient for many of the parents who don't have access to the internet at work, but can receive updates via Twitter SMS.

Various implementations of the subject matter described herein may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "information carrier" comprises a "machine-readable medium" that includes any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal, as well as a propagated machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a WAN, and the Internet.

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments.

Only a few implementations and examples are described and other implementations, enhancements and variations can be made based on what is described and illustrated in this application.

What is claimed is:

1. A monitoring system comprising:
a server; and
a plurality of monitoring devices, one monitoring device of the plurality of monitoring devices comprising:
a sensor bay comprising:
multiple sensors to monitor air quality modalities and generate corresponding monitored air quality data;
multiple interchangeable sensor boards to allow users to implement custom combinations of sensors, wherein each sensor is disposed on a corresponding one of the multiple interchangeable circuit boards; and
a motherboard coupled to the multiple interchangeable sensor boards through a common data and power bus shared by the multiple interchangeable sensor boards, wherein the motherboard relays messages among the multiple interchangeable sensor boards and supplies power to the multiple interchangeable sensor boards through the common data and power bus; and
a processor in communication with the multiple sensors to receive and process the monitored air quality data generated from the multiple sensors;
a cross-calibration system in communication with the processor to use data obtained from one sensor in the multiple sensors to continuously calibrate other sensors in the multiple sensors;
a display unit in communication with the processor to display the processed air quality data; and
a data communication unit to transmit the processed air quality data to the server; wherein the server is configured to provide a Web interface to allow users to review the monitored air quality data from the multiple monitoring devices, wherein the Web interface comprises a first graphical user interface widget to organize the multiple monitoring devices into one or more groups, and wherein the first graphical user interface widget comprises a neighborhood chart which identifies multiple sensors included in a user's neighborhood and compares contribution of each location in the user's neighborhood as a percent of a total pollution output of the user's neighborhood.

2. The monitoring device of claim 1, wherein the multiple sensors comprise at least two selected from the following: a light sensor, a temperature sensor, a humidity sensor, a noise sensor, a $CO_2$ sensor, and a volatile organic compound (VOC) sensor.

3. The monitoring device of claim 1, wherein the sensor bay comprises multiple circuit boards, wherein each sensor is disposed on a corresponding one of the multiple circuit boards.

4. The monitoring device of claim 3, wherein the sensory bay comprises interface slots to receive the multiple circuit boards with the corresponding sensors, and wherein the interface slots are configured to interchangeable receive different circuit boards with corresponding sensors.

5. The monitoring device of claim 1, comprising a display unit to present a level of each monitored air quality modality.

6. The monitoring device of claim 5, wherein the display unit comprises light emitting diodes (LEDs) arranged to show the level of each monitored air quality modality.

7. The monitoring device of claim 1, further comprising a position detector to detect a change in a location of the monitoring device.

8. A system comprising:
a server to receive and store monitored air quality data;
multiple monitoring devices in communication with the server to monitor air quality modalities, each monitoring device comprises
multiple sensors to monitor the air quality modalities and generate corresponding air quality data;
a processor in communication with the multiple sensors to receive and process the air quality data generated from the multiple sensors;
a display unit in communication with the processor to display the processed air quality data; and
a data communication unit to transmit the processed air quality data to a server as the monitored air quality data; and,
a cross-calibration system in communication with the processor to use data obtained from one sensor in the multiple sensors to continuously calibrate other sensors in the multiple sensors;
wherein the server is configured to provide a Web interface to allow users to review the monitored air quality data from the multiple monitoring devices, wherein the Web interface comprises a first graphical user interface widget to organize the multiple monitoring devices into one or more groups, and wherein the first graphical user interface widget comprises a neighborhood chart which identifies multiple sensors included in a user's neighborhood and compares contribution of each location in the user's neighborhood as a percent of a total pollution output of the user's neighborhood.

9. The system of claim 8, wherein the server is configured to provide a Web interface to allow users to review the monitored air quality data from the multiple monitoring devices.

10. The system of claim 9, wherein the Web interface comprises:
a first graphical user interface widget to organize the multiple monitoring devices into one or more groups.

11. The system of claim 10, wherein the graphical user interface widget to organize the multiple monitoring devices into one or more groups comprises:
an indication of total pollution for each group; and
a contribution of each monitoring device in each group.

12. The system of claim 10, wherein the Web interface comprises:
a second graphical user interface widget to display a time-dependent pattern of at least one of the monitored air quality modalities.

13. The system of claim 9, wherein the Web interface comprises:
a third graphical user interface widget to allow users to conduct on-line discussions.

14. A method comprising:
receiving, at a server, monitored air quality data from each of multiple sensor devices, wherein the monitored air quality data from at least one of the sensor devices comprises multiple air quality modalities monitored using multiple sensors
at a cross-calibration system, using data obtained from a first sensor in the multiple sensors to continuously calibrate other sensors in the multiple sensors to determine accuracy of the multiple sensors;
storing, at the server, the received monitored air quality data;
presenting, from the server, a graphical user interface to receive user input to organize the received monitored air quality data into one or more groups;
organizing the received monitored air quality data from the multiple sensor device devices into the one or more groups based on the received user input; and
displaying the received monitored air quality data organized into the one or more groups; the method further comprising:
configuring the server to provide a Web interface to allow users to review the monitored air quality data from the multiple sensor devices, wherein the Web interface comprises a first graphical user interface widget to organize the multiple sensor devices into one or more groups, and wherein the first graphical user interface widget comprises a neighborhood chart which identifies multiple sensors included in a user's neighborhood and compares contribution of each location in the user's neighborhood as a percent of a total pollution output of the user's neighborhood.

15. The method of claim 14, wherein displaying the received monitored air quality data organized into the one or more groups comprises:
displaying total pollution for each group; and
displaying a contribution of each sensor device in each group to the total pollution.

16. The method of claim 15, wherein displaying the received monitored air quality data organized into the one or more groups comprises:
displaying a breakdown of the different air quality modalities.

17. The method of claim 14, wherein the multiple sensors are configured to monitor at least two selected from the following: light, temperature, humidity, noise, CO2 and volatile organic compounds (VOC).

18. The method of claim 14, wherein the graphical user interface comprises a widget to allow two or more users to conduct an on-line discussion.

19. The method of claim 14, wherein the graphical user interface comprises:
a widget to organize the multiple sensor devices into one or more groups.

20. The method of claim 19, wherein the graphical user interface widget to organize the multiple sensor devices into one or more groups comprises:
an indication of total pollution for each group; and
a contribution of each monitoring device in each group.

21. The method of claim 14, comprising displaying a time-dependent pattern of at least one of the monitored air quality modalities.

22. The method of claim 14, wherein continuously calibrating other sensors in the multiple sensors includes calibrating the other sensors periodically at a set period of time.

23. The method of claim 14, wherein continuously calibrating other sensors in the multiple sensors includes calibrating the other sensors each time a reading of the first sensor is obtained.

24. The method of claim 14, wherein continuously calibrating other sensors in the multiple sensors includes calibrating the other sensors each time the server or a user requests calibration.

* * * * *